United States Patent
Pilgrimm

(12) 
(10) Patent No.: US 6,638,494 B1
(45) Date of Patent: Oct. 28, 2003

(54) SUPER-PARAMAGNETIC PARTICLES WITH INCREASED $R_1$ RELAXIVITY, PROCESS FOR PRODUCING SAID PARTICLES AND USE THEREOF

(76) Inventor: Herbert Pilgrimm, Sophie-Charlotte-Str.27a, D-14050 Berlin (DE)

( * ) Notice: Subject to any disclaimer, the term of this patent is extended or adjusted under 35 U.S.C. 154(b) by 30 days.

(21) Appl. No.: 09/716,709

(22) Filed: Nov. 20, 2000

Related U.S. Application Data

(63) Continuation-in-part of application No. 09/142,422, filed as application No. PCT/DE97/00578 on Mar. 13, 1997, now abandoned.

(30) Foreign Application Priority Data

Mar. 18, 1996 (DE) ......................................... 196 12 001

(51) Int. Cl.$^7$ ............................. A61B 5/055; A61K 9/16
(52) U.S. Cl. ................ 424/9.323; 424/9.32; 424/9.322; 424/490
(58) Field of Search .................. 424/9.3, 9.32, 424/9.322, 9.323, 9.36, 489, 490, 491, 498, 493; 436/173

(56) References Cited

U.S. PATENT DOCUMENTS

| | | | | |
|---|---|---|---|---|
| 5,928,958 A | * | 7/1999 | Pilgrimm | .................... 436/526 |
| 6,348,338 B1 | * | 2/2002 | Wittig et al. | .............. 435/172.1 |

FOREIGN PATENT DOCUMENTS

| | | |
|---|---|---|
| EP | 284 549 | 9/1988 |
| EP | 580878 | 2/1994 |
| WO | WO90/01899 | 3/1989 |
| WO | WO89/11154 | 11/1989 |
| WO | WO90/07380 | 7/1990 |
| WO | WO96/03653 A1 * | 2/1996 .......... G01N/33/543 |
| WO | WO96/09840 A1 * | 4/1996 ........... A61K/49/00 |

OTHER PUBLICATIONS

Eck et al., "Gene–based therapy." Goodman & Gillman's The Pharmacological Basis of Therapeutics– Ninth Edition, McGraw–Hill: 77–101, 1996.*
Deonarain M., "Ligand–targeted receptor–mediated vectors for gene delivery." Exp. Opin. Ther. Patents, vol. 8 (1):53–69, 1998.*
Crystal R., "Transfer of genes to humans: Early lessons and obstacles to success." Science, vol. 270: 404–410, 1995.*
Miller et al., "Targeted vectors for gene therapy." FASEB, vol. 9:190–199, Feb. 1995.*

* cited by examiner

*Primary Examiner*—Michael G. Hartley
(74) *Attorney, Agent, or Firm*—Collard & Roe, P.C.

(57) ABSTRACT

The invention relates to super-paramagnetic single domain particles with increased $R_1$ relaxivity and with surface-stabilizer substances. The particles are characterized in that they consist of iron hydroxide, ferric hydrate, iron oxide, iron mixed oxide or iron; are between 1 and 10 nm in size, the mean particle diameter $d_{50}$ being 2–4 nm; and have increased $R_1$ relaxivity of between 2 and 50, the ratio of the relaxivities $R_2/R_1$ being less than 5. Stabilizer substances of special carboxylic acids are bound to the particle surfaces; these prevent aggregation and sedimentation under gravity or in a magnetic field. If necessary, the particles can also contain further known stabilizer substances and other pharmacological substances. The novel particles can be used for attacking tumors, boosting immunity, for cell fusion, gene transfer, or as contrasting agents in magnetic resonance diagnostics using magnetic fields where necessary.

7 Claims, No Drawings

SUPER-PARAMAGNETIC PARTICLES WITH INCREASED $R_1$ RELAXIVITY, PROCESS FOR PRODUCING SAID PARTICLES AND USE THEREOF

CROSS-REFERENCE TO RELATED APPLICATION

This is a Continuation-in-Part of U.S. Pat. No. 09/142,422, filed Sep. 4, 1998, now abandoned, which is a 371 of PCT/DE97/00578 filed Mar. 13, 1997.

BACKGROUND OF THE INVENTION

1. Field of the Invention

This invention concerns super-paramagnetic particles with an increased $R_1$ relaxivity which can be used as diagnostics in NMR tomography and as a pharmacologically active substance. This invention also concerns a production process and the use of the new particles.

2. The Prior Art

European Patent No B 284,549 describes super-paramagnetic single-domain particles of iron oxide, mixed iron oxides or iron with a particle size in the range between 3 and 20 nanometers, having organic substances of the group consisting of polyalkylene glycols containing phosphate groups, diphosphate groups, polyphosphate groups, thiophosphate groups, phosphonate groups or thiophosphonate groups, nucleotides containing phosphate groups, their oligomers or polymers and phosphate group-containing carbohydrates chemically bound at their surface, optionally having additional binding sites.

German Patent No. DE-A-4,309,333 describes stable, degradable aggregates with a particle size in the range between 10 and 1000 nanometers with defined behaviour in the magnetic field, with the aggregates consisting of multiple small super-paramagnetic single-domain particles of iron oxide, mixed iron oxides or iron with a particle size in the range between 3 and 20 nanometers, having substances of the group of polyalkylene glycols containing phosphate groups, diphosphate groups, polyphosphate groups, thiophosphate groups, phosphonate groups or thiophosphonate groups, or having carbohydrates or phosphate group-containing nucleotides their oligomers or polymers chemically bound at their surface.

WO 96/03653 describes super-paramagnetic particles consisting of super-paramagnetic single-domain particles and aggregates of super-paramagnetic single-domain particles having organic substances bound at their surface. The super-paramagnetic particles are composed of a mixture of small super-paramagnetic single-domain particles with a particle size in the range between 3 and 50 nanometers and stable, degradable aggregates of small super-paramagnetic single-domain particles with a particle size in the range between 10 and 1000 nanometers and consist of iron hydroxide, iron oxide hydrate, iron oxide mixed iron oxides or iron having mono- and/or polyhydroxyl group-containing aromatic substances, polyglycerols, amino acid-containing substances, silicate group-containing substances of orthosilicic acid and their condensation products and phosphate group-containing substances of ortho- or meta-phosphoric acid and their condensation products bound at their surface.

Super-paramagnetic single-domain particles with a particle size in the range between 3 and 50 nanometers can be produced according to the state of the art and used, for example, as contrast media for NMR tomography, with preferred particle diameters in the range of 5–20 nm. In the regions of the body where these particles have accumulated, they lead to a greater shortening of the 2-relaxation time, and to darkening of the signal. Therefore, one also speaks of "negative" NMR contrast media with super-paramagnetic single-domain particles. The T relaxation time is inversely proportional to the relaxivity R, so the relaxivity R increases as the T relaxation time is shortened. The $T_2$ relaxation time has a linear dependence on the particle diameter of the magnetic particles. The larger the particle diameter, the greater the shortening of the $T_2$ relaxation time and the lower the required particle concentration to achieve a "negative" contrast. The contrast medium demand is in the range of 10 to 20 mmol Fe/kg body mass, and thus is much lower in comparison with the "positive" NMR contract media based on gadolinium chelates used in the past.

The $T_1$ relaxation time of such "negative" contrast media is not shortened greatly, so that there is no mentionable signal amplification in the NMR tomography in the body regions where they have accumulated. There is little lightening of the signal in the tissue. For many applications, it would be advantageous to be able to use super-paramagnetic single-domain particles with an increased "positive" NMR contrast medium effect.

If $T_1$-weighted NMR tomography is to be performed, then the ratio of the relaxivities $R_2/R_1$ must be as small as possible, but at least smaller than 5.

The $R_1$ relaxivity cannot be changed much with a reduction in particle diameter, but the $R_2$ relaxivity can be reduced. With very small super-paramagnetic single-domain particles, the ratio of relaxivities $R_2/R_1$ is reduced so greatly that $T_1$-weighted NMR tomography can be performed. Since super-paramagnetic single-domain particles have an influence on signal intensity even in very low concentrations, they can be superior to the paramagnetic contrast media used in the past.

SUMMARY OF THE INVENTION

The object of the present invention is to develop very small super-paramagnetic single-domain particles which can be used as contrast media for $T_1$-weighted NMR tomography, for example.

According to this invention, this can be achieved by super-paramagnetic single-domain particles with an increased $R_1$ relaxivity and with surface stabilizer substances, comprising particles of iron hydroxide, iron oxide hydrate, iron oxide, mixed iron oxides or iron with a particle size in the range between one and ten nanometers, with an average particle diameter $d_{50}$ of two to four nanometers, an increased $R_1$ relaxivity in the range of two to fifty, an $R_2/R_1$ relaxivity ratio of less than five, and having stabilizer substances on their surface of aliphatic dicarboxylic acids, aliphatic polycarboxylic acids substitution products thereof and derivatives thereof. That stabilizer substances prevent aggregation and sedimentation of the particles in a gravitational field or a magnetic field. On the stabilized particles are optionally bound further stabilizer substances, tissue-specific binding substances, pharmacologically active substances, pharmacologically active cells, pharmacologically active chelating agents, cell fusion mediating substances or gene transfer mediating substances, as well as mixtures thereof.

DETAILED DESCRIPTION OF THE PREFERRED EMBODIMENTS

The super-paramagnetic single-domain particles of the invention with an increased $R_1$ relaxivity have on its surface first stabilizer substances.

If the first stabilizing substances are aliphatic dicarboxylic acids they are preferably malic acid, tartaric acid, glucaric acid.

If the first stabilizing substances are aliphatic polycarboxylic acids they are preferably citric acid, cyclohexanetricarboxlic acid, cyclohexanehexacarboxylic acid, ethylenediaminetetraacetic acid or diethylenetriaminepentaacetic acid.

Substitution products of dicarboxylic or polycarboxylic acids are compounds with unchanged carboxyl groups but one or more replaced hydrogen atoms by alkyl groups, halogen atoms or other groups such as citramalic acid, 2-methylene malic acid, alpha-hydroxycitric acid, aspartic acid, glutamic acid, pteroglutamic acid (folic acid).

Derivatives of dicarboxylic or polycarboxylic acids are compounds produced by changing of the carboxyl group such as esters, acid chlorides, anhydrides, amides, hydroxamic acids, imido esters, e.g. preferred $C_{12}$–$C_{18}$ fatty acid esters with one or more of the a.m. dicarboxylic or polycarboxylic acids such as citric acid stearyl ester.

Various possibilities of achieving the goal of the invention—very small superparamagnetic particles for e.g. T1-weighted tomography—have been found:

1. By reducing the magnetic susceptibility of the super-paramagnetic single-domain particles;
2. By reducing the particle diameter of the super-paramagnetic single-domain particles in the range of 1–10 nm, preferably in the range of 2–4 nm;
3. Through the choice of stabilizer substances, and
4. Through the thickness and the water content of the stabilizer substance layer.

The very small super-paramagnetic single-domain particles may consist of the following substances: iron hydroxide, iron oxide hydrate, $\gamma$-$Fe_2O_3$, $Fe_3O_4$, the mixed iron oxides of the general formula m $MO$.n $Fe_2O_3$, where M denotes the divalent metal ions Fe, Co, Ni, Mn, Be, Mg, Ca, Ba, Sr, Cu, Zn, Pt or mixtures thereof, the mixed oxides of the general formula m $Fe_2O_3$.n $Me_2O_3$, where Me denotes the trivalent metal ions Al, Cr, Bi, rare earth metals or mixtures thereof or iron, and m and n denote integers from 1 to 6. Thus, through the composition and structure of the single-domain particles, their magnetic susceptibility can be varied in a wide range, and an $R_2/R_1$ relaxivity ratio of less than 5 can be established. However, it is important for use in medicine to take into account the toxicity of the individual components of the single-domain particles.

The super-paramagnetic particles of the invention are preventing aggregation and sedimentation in a gravitational field or in a magnetic field. That means the aggregation and sedimentation of the particles is prevented in a gravitational field up to 10,000 g for at least 10 minutes, such as during centrifugation with 10,000 rpm (see example 1). The aggregation and sedimentation is prevented also in a magnetic field of about 0.1 Tesla for 30 minutes and for above defined iron/iron oxide particles of 1–10 nm diameter. Said particles of <5 nm are even stable against aggregation and sedimentation in a magnetic field of e.g. about 1 Tesla for 30 minutes. That are usual conditions of an NMR tomography apparatus.

The average particle diameter "$d_{50}$" means that at least 50% of the particles has the diameter 2–4 nm and the other has a diameter <2 nm and between 4 and 10 nm.

The magnetic susceptibility of the very small super-paramagnetic single-domain particles according to the present invention can also be adjusted in a wide range, from approximately 1 to 100 EMU/g, through the composition of the iron salt solution and its method of preparation.

It has surprisingly been found that a change in composition of the iron salt solution has an influence on the $R_2/R_1$ relaxivity ratio. The magnetic susceptibility can be reduced from approximately 100 EMU/g to approximately 20 EMU/g by increasing the $Fe^{3+}/Fe^{2+}$ concentration ratio of the iron salt solution from 2 to 10.

Optionally a change in $R_2/R_1$ relaxivity ratio can be achieved by an oxidation or reduction reaction after precipitation of the very small single-domain particles. Suitable redox agents include, for example, nitrate ions, hydrogen peroxide, hydroxylamine, ascorbic acid.

It has surprisingly been found that the particle size of the super-paramagnetic single-domain particles can be reduced even further by precipitating the particles under an elevated temperature and optionally an elevated pressure, with bases from an iron salt solution containing aqueous or water-miscible organic solvents, adding a solution of a described carboxylic acid stabilizer substance in water or water-miscible organic solvent immediately before, during or immediately after precipitation, or by precipitating with a mixture of stabilizer substance and base, or if the stabilizer substance is also a base, by just adding the organic base. A precipitation temperature of 50° C. to 120° C. can be stipulated as advantageous. At temperatures above 100° C., the or is carried out in autoclaves. Adding the stabilizer substance immediately before, during or immediately after precipitation prevents the above-mentioned redox reactions and yields very small super-paramagnetic single-domain particles.

The particle size of the very small super-paramagnetic single-domain particles is in the range of 1 to 10 nm, especially in the range of the average particle diameter $d_{50}$ of 2 to 4 nm. The stated particle sizes of 1 to 10 nm with an average particle diameter $d_{50}$ of 2–4 nm always refers to the particles without stabilizer substance.

With a reduction in particle size, the biological tolerability is also improved, and the rate of degradation in the body is increased. The bioavailability of the very small super-paramagnetic particles in the body is a few hours to days, depending on the particle size and the composition of the stabilizer substances, i.e., the reticuloendothelial system binds the very small super-paramagnetic particles relatively slowly.

The object of the present invention is also to expand the range of substances that stabilize the very small super-paramagnetic single-domain particles against aggregation and sedimentation, to optimally adapt the physicochemical and physiological properties of the corresponding magnetic particles to the respective applications, and these substances should be stable and easily synthesized.

It has surprisingly been found that even small molecules, not only the relatively large polymer molecules or macromolecules known in the state of the art, are suitable for stabilization of very small super-paramagnetic single-domain particles.

It has been found that aliphatic di- and polycarboxylic acids and their substitution products and derivatives, such as malic acid, tartaric acid, citric acid, aspartic acid, are suitable stabilizer substances for very small super-paramagnetic single-domain particles.

The very small super-paramagnetic single-domain particles according to this invention, stabilized with citric acid, for example, have much smaller diameters than the smallest super-paramagnetic iron oxides which were provided with a polymer coating and were produced in the past. Thus, for example, it is now possible to produce stabilized super-paramagnetic single-domain particles with an average particle diameter $d_{50}$ range of 2 to 4 nm that can be filtered through a 100,000 D filter, i.e., they have an average particle diameter of the stabilized particles of 4 to 8 nm. The $R_2/R_1$ relaxivity ratios can thus be reduced to values between 1 and 3.

Thus, the half-life of the novel, very small, superparamagnetic single-domain particles in blood is much longer than that of previous particles, thereby greatly expanding the possible areas of use for T1-weighted NMR tomography e.g. angiography and for diagnosis of thrombi, tumors and inflamed tissues, or for T2-weighted tomography e.g. lymphography and for diagnosis of thrombi, tumors and inflamed tissues, or for T1- and T2-weighted tomography e.g. differentiation diagnostic by use of T1- and T2-weighted images.

It has surprisingly also been found that the type and quantity of stabilizer substances have an influence on the $R_2/R_1$ relaxivity ratio of the super-paramagnetic single-domain particles. For example, $R_2/R_1$ can be reduced by an increase in the hydrophilic nature of the stabilizer and thus its degree of hydration. The quantity of stabilizer substance also has an influence on particle size. With an increase in the concentration of the stabilizer substance, the particle diameter becomes smaller.

The physicochemical and physiological properties of the resulting very small super-paramagnetic single-domain particles can be optimized for the respective application if additional (further) stabilizer substances are bound at the surface of the particles, i.e. at the first stabilizer substances. These additional stabilizer substances can be selected from aromatic substances containing mono- and polyhydroxyl groups, such as benzenoids, coumarins, lignans, terphenyl, flavonoids, tannins, xanthones, benzophenones, naphthalenes, naphthoquinones, anthraquinones, anthracyclines, polycyclic condensed aromatic compounds and their derivatives; substances containing amino acids, such as albumins, globulins, oligopeptides, polypeptides, denatured products of proteins and proteids, such as gelatins, casein hydrolysate, gluteline; substances containing thio groups, such as mercaptopurine, mercaptocytosine, mercaptoguanine, mercaptouracil, mercaptothymine, mercaptohypoxanthine, and their mercaptonucleosides and mercaptodeoxynucleosides; substances of ortho-silicic acid containing silicate groups and their condensation products with divalent and polyvalent inorganic ions and organic acids, such as phytic acid, alginic acid, gallic acid; substances of ortho- or meta-phosphoric acid containing phosphate groups and their condensation products, such as pyrophosphoric acid, polyphosphoric acids, cyclophosphates and their heterocondensation products, and their reaction products with organic compounds containing basic groups, such as spermine, spermidine, polyethyleneimine, protamines, oxygelatin and their derivatives; organic substances of the group consisting of carbohydrates containing phosphate groups, di-phosphate groups, polyphosphate groups, thiophosphate groups, phosphonate groups, thiophosphonate groups, carboxylate groups, sulfate groups, sulfonate groups, mercapto groups, silanetriol groups; polyalkylene glycols, alkyl, aryl and/or alkylaryl polyethylene glycols; nucleotides that contain phosphate groups, as well as their oligomers or polymers; polysaccharides containing nitrogen, such as mucopolysaccharides, glycoproteids, chitins and their derivatives.

The stabilizer substances can be produced by the state of the art or they can be acquired commercially.

To the first or further stabilizer molecules may be bound all tissue-specific binding substances such as antigens, antibodies, ribonucleic acids, deoxyribonucleic acids, ribonucleic acid sequences, deoxyribonucleic acid sequences, haptenes, avidin, streptavidin, protein A, protein G, endotoxin-binding proteins, lectins, selectins, surface proteins of organelles; viruses, microbes, algae, fungi; all pharmacologically active substances such as anti-tumor proteins, enzymes, anti-tumor enzymes, antibiotics, plant alkaloids, alkylating reagents, antimetabolites, hormones and hormone antagonists, interleukins, interferones, growth factors, tumor necrosis factors, endotoxins, lymphotoxins, urokinase, streptokinase, plasminogen streptokinase activator complex, tissue plasminogen activators, desmodus plasminogen activators, macrophage activation bodies, antisera, blood and cell constituents and their degradation products and derivatives, cell wall components of organelles, viruses, microbes, algae, fungi and their degradation products and derivatives, protease inhibitors, alkyl phosphocholines, substances containing radioactive isotopes, surfactants, cardiovascular pharmaceuticals, chemotherapeutics, gastrointestinal pharmaceuticals, neuropharmaceuticals; all pharmacologically active cells such as organelles, viruses, microbes, algae, fungi, especially red blood cells, platelets, granulocytes, monocytes, lymphocytes, islets of Langerhans;

all pharmacologically active chelating agents, such as polycarboxylic acids, polyamino acids, porphyrins, catecholamines;

all substances that promote cell fusion, such as polyethylene glycols, alkyl, aryl and alkylaryl polyethylene glycols and their derivatives;

all substances that mediate gene transfer, such as polyethylene glycol and derivatives thereof; polyamine compounds such as polyethyleneimine, spermine, spermidine, protamine sulfate; as well as mixtures thereof.

There are two possibilities in the state of the art for stabilizing super-paramagnetic particles produced by precipitation reactions against aggregation and sedimentation:

1. The super-paramagnetic particles are prepared by precipitation from the iron salt solutions, purified and then stabilized with the proper stabilizer substance, or 2. The stabilizer substances are mixed with the iron salt solutions and the mixture is heated to the respective precipitation temperature and precipitation is performed.

Since the mixture of $Fe^{3+}/Fe^{2+}$ salt solution is a reactive redox system, parts of the stabilizer substance may be oxidized or reduced, and the $Fe^{3+}/Fe^{2+}$ concentration ratio changes in an unreproducible manner. Many possible stabilizer substances or even many organic anions of the iron salt solutions form complexes with the iron salts which also lead to non-magnetic or unreproducible precipitation products.

The method of producing very small super-paramagnetic single-domain particles with an increased $R_1$ relaxivity and with surface stabilizer substances is performed from an iron salt solution at an elevated temperature in the range of 50° C. to 120° C., with the particles being precipitated with bases, e.g., with alkali lye, ammonia water or organic bases. When the temperatures is greater than 100° C., the process is carried out in an autoclave. The precipitation can also be performed with a mixture of stabilizer substance and base, or, if the stabilizer substance is also a base, it can be performed only by adding the organic base. Organic bases, which function as the stabilizer substance at the same time include, for example, polyethyleneimine, spermine, spermidine or protamine. A dissolved stabilizer substance consisting of aliphatic di- and polycarboxylic acids and their substitution products and derivatives such as malic acid, tartaric acid, citric acid, aspartic acid is added to the iron salt solution during precipitation or immediately after precipitation in an amount of 5 to 100 wt %, based on the quantity of single-domain particles.

By adding an oxidizing agent or reducing agent, the $Fe^{3+}/Fe^{2+}$ concentration ratio in the precipitated product can be adjusted in the range from one to infinite ($\gamma$-$Fe_2O_3$) to achieve the desired change in $R_2/R_1$ relaxivities. The dispersion of very small, stabilized super-paramagnetic particles prepared in this way is cooled and neutralized with hydrochloric acid, for example, the dispersion is dialyzed until the electric conductivity of the filtrate is <10 mS/cm.

With some stabilizer substances, it is necessary to input more energy, e.g., by the action of ultrasound, to prepare stable dispersions. The stable dispersion may also contain larger or weakly aggregated super-paramagnetic single-domain particles, which can easily be separated from the very small super-paramagnetic particles by sedimenting them in a magnetic field or by centrifugation. Optionally additional substances of the group of further stabilizer substances, tissue-specific binding substances, pharmacologically active substances, pharmacologically active cells, pharmacologically active chelating agents, cell fusion mediating substances and gene transfer mediating substances, as well as mixtures thereof to which the very small stabilized super-paramagnetic single-domain particles are coupled.

Tissue-specific binding substances are substances such as rutin which in a mixture with e.g. citric acid is bound to the surface of the superparamagnetic particles as a new stabilized preparation having very good binding characteristics to the cell wall parts of e.g. tumor cells. It has been found that after injection of such a preparation on rats the tumor growth reduced half the time (see example 9).

Further it has been found that superparamagnetic particles of the present invention stabilized with an aliphatic carboxylic acid such as citric acid are added on neutrophilic white blood cells as a representative of the group of pharmacologic active cells. The "magnetizable" white blood cells enriches also in inflamed tissue and can be used as contrast medium in NMR for the recognition of inflamed tissue. These "magnetizable" white blood cells enriches also on tumor edges and can be used as contrast medium in NMR for the recognition of tumors. The addition of stabilized superparamagnetic particles on pharmacological active cells takes place ex vivo by mixing the stabilized particles with a blood sample or with a fraction thereof enriched with leucocytes. After an incubation time of about 20 min the injection of the blood sample into the body follows. The NMR contrast effect can be observed after 5–120 min (see ex. 10).

Further it has been found that superparamagnetic particles of the present invention stabilized e.g. with citric acid and tannin bind also on leucocytes. After i.v. injection of a stabilized watery particle dispersion they enrich in the lymphatic node and in the bone marrow. After about 12–24 h the lymphatic node and the bone marrow are visible in a NMR image. Pharmacological effects of the "magnetizable" blood cells are to achieve by heating the strong inhomogenic electromagnetic fields (magnetic field hyperthermie) or by coupling on pharmacologic active substances and/or by radiation with radioactive or particle radiation.

With respect to cell fusion mediating substances and gene transfer mediating substances it is possible to bind on super-paramagnetic particles, stabilized by e.g. an aliphatic carboxylic acid, substances such as methoxy polyethylene glycolphosphate (molecular weight 2000). With such particles cell fusion and gene transfer can be recognized optically by microscoping the cells in the presence of the dark colored magnetic particles, i.e. dark coloring of the cells.

Genes which are to transport by invasion into the cells are mixed with an surplus of superparamagnetic particles stabilized with e.g. an aliphatic carboxylic acid and methoxy polyethylene glycolphosphate (MW 2000) to wrap up the genes with the particles. Not bounded particles are removed by washing with a physiologically acceptable solution. These "magnetized genes" are added to the cell. By microscopy the skilled in the art is able to recognize the dark coloring of the cell content. After i.v. injection of a watery suspension of the "magnetized genes" they enrich in the lymphatic node and in the bone marrow.

Preparation of the very small super-paramagnetic particles according to the present invention is explained here on the basis of examples.

EXAMPLES

Example 1

Iron(III) chloride (270 g) and iron(II) chloride (119 g) are dissolved in one liter of distilled water while stirring and heated to 100° C. in the absence of oxygen. By adding a mixture of ammonia water and 35 g citric acid, the pH of the solution is adjusted to 10 while stirring and the mixture is boiled for ten minutes. Then the dispersion is cooled to approx. 20° C., adjusted to a pH of 7.0 with hydrochloric acid and dialyzed with distilled water until the dialysate has an electric conductivity of <10 $\mu$S/cm, and then dispersed for twenty minutes with ultrasound and 300 W power. To remove larger particles or weakly aggregated super-paramagnetic particles, the dispersion is centrifuged for ten minutes at 10,000 rpm. The very small super-paramagnetic particles can be mixed with physiological saline solution for use as a positive i.v. contrast medium for NMR diagnostics.

Example 2

100 mL of the dispersion of very small super-paramagnetic single-domain particles from Example 1, with a magnetic saturation induction of 10 mT, are mixed with a solution consisting of 4 g methoxy polyethylene glycol phosphate (molecular weight 1000), 1 g rutin and 50 mL methanol, and the methanol is distilled off in vacuo. Water is added to the dispersion to yield 100 mL, sodium hydroxide is added to adjust the pH to 7.0; the mixture is then dispersed for ten minutes ultrasonically at a power of 100 W, and then centrifuged for ten minutes at 10,000 rpm to remove larger particles or weakly aggregated super-paramagnetic single-domain particles. The very small super-paramagnetic particles can be used as a positive i.v. contrast medium for angiography in NMR diagnostics.

Example 3

20 mL of the dispersion of very small super-paramagnetic single-domain particles from Example 2, with a magnetic saturation induction of 1 mT are mixed with a solution of 10 mg doxorubicin in 10 mL physiological saline solution. These very small super-paramagnetic particles are suitable for accumulating in tumors and attacking said tumors.

Example 4

Iron(III) chloride (50.3 g) and iron(II) sulfate (139 g) are dissolved in one liter of distilled water while stirring and heated to 85° C. in the absence of oxygen. While adding 25% ammonium hydroxide solution by drops, a pH of 10.5 is established. Immediately after precipitation, the dispersion is mixed with a solution of 5 g L-aspartic acid and 25 g tartaric acid in 500 mL water and stirred for twenty minutes at 85° C. Then the dispersion is cooled to approx. 20° C., adjusted to a pH of 7.0 with hydrochloric acid, mixed with 20 mL 30% hydrogen peroxide and stirred until there is no more evolution of gas. The dispersion is next dispersed ultrasonically for twenty minutes at a power of 300 W and then dialyzed until the dialysate has an electrical conductivity of <10 $\mu$S/cm. To remove larger particles or weakly aggregated super-paramagnetic particles, the dispersion is centrifuged for ten minutes at 10,000 rpm. The very small super-paramagnetic particles can be used as a positive i.v. contrast medium for angiography in NMR diagnostics.

Example 5

100 mL of the dispersion of the very small superparamagnetic single-domain particles from Example 4, with a magnetic saturation induction of 5 mT, mixed with a solution of 4 g methoxypolyethylene glycol phosphate (molecular weight 2000) and 0.4 g lauryloxypolyethylene glycol (molecular weight 1000) in 50 mL water. The very small super-paramagnetic particles can be mixed with physiological saline solution for use as a contrast medium for lymphography and for tumor diagnostics in NMR diagnostics.

Example 6

100 mL of the dispersion of the very small superparamagnetic single-domain particles from Example 4, with a magnetic saturation induction of 5 mT, are mixed with a solution of 1 g oxygelatin in 50 mL water. The very small super-paramagnetic particles can be mixed with physiological oxygelatin solution for use as a contrast medium for lymphography and for tumor diagnostics in NMR diagnostics.

Example 7

Iron(III) chloride (50.3 g) and iron(II) sulfate (139 g) are dissolved in one liter of distilled water while stirring and heated to 100° C. in the absence of oxygen. During dropwise addition of 25% ammonium hydroxide solution, a pH of 10.5 is established. Immediately after precipitating, the dispersion is mixed with a solution of 40 g malic acid in 500 mL water and stirred for ten minutes at 100° C. Then the dispersion is cooled to approx. 20° C., its pH is adjusted to 7.0 with hydrochloric acid, and it is mixed with 20 mL 30% hydrogen peroxide and stirred until there is no more evolution of gas. The dispersion is next dispersed ultrasonically for twenty minutes at a power of 300 W and then dialyzed until the dialysate has an electrical conductivity of <10 $\mu$S/cm. To remove larger particles and weakly aggregated super-paramagnetic particles, the dispersion is centrifuged for ten minutes at 10,000 rpm. The very small, super-paramagnetic particles can be used as a positive i.v. contrast medium for angiography in NMR diagnostics.

Example 8

100 mL of the dispersion of very small superparamagnetic single-domain particles from Example 7, with a magnetic saturation induction of 5 mT, are mixed with a solution of 4 g spermidine in 50 mL water. The very small super-paramagnetic particles can be mixed with solutions of nucleotides containing phosphate groups, oligomers thereof or polymers thereof for the purpose of gene transfer.

Typical analytical data on the very small superparamagnetic single-domain particles of example 1–8 include:
particle diameter $d_{50}$: 4 nm
total diameter with stabilizer: 8 nm
iron(II) content: 6%
T1 relaxivity: 30 L/mmol·s
T2 relaxivity: 56 L/mmol·s
$R_2/R_1$ relaxivity ratio: 1.87

Example 9

10 ml of a dispersion of superparamagnetic single-domain particles from example 1 with a particle diameter $d_{50}$ of 4 nm with an iron content of 0.5 mmol Fe/10 kg body weight are mixed with 10 ml of blood. After a time of 20 min. this mixture is intravenously splashed into the body. The mixture accumulates the very small superparamagnetic particles in tumors and in inflamed tissue. The NMR contrast can be observed after 5–120 min.

Example 10

10 ml of a dispersion of superparamagnetic single-domain particles from example 2 with a particle diameter $d_{50}$ of 4 nm and with an iron content of 0.5 mmol Fe/10 kg body weight are mixed with 1 ml lysate of 0.1 g tumor cells. The lysate of tumor cells is produced by an ultrasonic treatment of 50 W power for 10 min. This mixture is used for the incorporation of surface proteins and gene fragments of the tumor cells through the reticuloendothelial system into the body. The answer of the body is an immunological reaction to the components of the tumor.

Example 11

10 ml of a dispersion of superparamagnetic single-domain particles from example 1 with a particle diameter $d_{50}$ of 4 nm and with an iron content of 0.5 mmol Fe/10 kg body weight are mixed with 1 ml 10% Na-salt of tannin (pH value 7). After 20 min. the not bound part of tannin is removed by dialysis with a physiological acceptable solution. This mixture is used for accumulating superparamagnetic particles in the lymphatic node and in the bone marrow by i.v. injection. The NMR contrast effect is observed after 12–24 hrs in T1-weighted or T2-weighted NMR tomography.

Example 12

10 ml of a dispersion of superparamagnetic single-domain particles from example 2 with a particle diameter $d_{50}$ of 4 nm and with an iron content of 0.5 mmol Fe/10 kg body weight are mixed with 1 g polyethylene glycol (MW 2000). The excess part of PEG is removed by a dialysis trough a 5000 k Dalton filter. A surplus of the mixture of superparamagnetic particles with the further stabilizer substance polyethylene glycol is mixed with 10 $\mu$g genes of adenosine deaminase cDNA which are to transport by invasion into the cells of peripheral blood lymphocytes. After 20 min. the not bound part of polyethylene glycol is removed by dialysis with a physiologically acceptable salt solution. The "magnetized" genes are added to the cells of said lymphocytes.

The cell content turns dark by the dark colored "magnetized" genes. The cells with the "magnetized" genes are injected intramuscular in the body. Now the changed cells will be involved in the usual regeneration process and will express the newly included genes.

The main areas for use of the very small superparamagnetic particles according to the present invention is in the fields of NMR contrast media for angiography, lymphography, diagnosis of thrombi and tumors, destroying tumors, dissolving thrombi, boosting immunity, mediating cell fusion or gene transfer, where the efficacy of the tumor treatment, thrombolysis, cell fusion and gene transfer can be determined with NMR diagnostics.

The very small super-paramagnetic single-domain particles can be used for tumor diagnostics because when they are injected into the blood stream, an accumulation can be observed, especially of the very small super-paramagnetic single-domain particles stabilized with methoxy polyethylene glycol phosphate or phosphonate, in the tumors.

By coupling pharmacologically effective substances to the very small super-paramagnetic single-domain particles, the concentration of these particles at the site of action can be increased, especially with the very small super-paramagnetic single-domain particles stabilized with methoxy polyethylene glycol phosphate or phosphonate or when using tumor-specific antibodies. This circumstance is important in cancer therapy, because the substances used for chemotherapy of tumors have very strong side effects on the entire body, and the rest of the patient's body is not stressed so greatly with cytostatics when the latter are concentrated at the site of action.

In animal experiments, good effects have been obtained with these particles as parenteral positive contrast media in T1-weighted NMR tomography, such as that used for blood circulation, for diagnosis of thrombi and tumors, for imaging the gastrointestinal tract, and as antibody-specific contrast media. The high blood half-life has a positive effect here because the reticuloendothelial system absorbs the particles slowly, and especially when the particles are coupled to anti-bodies, they are mobile in the blood stream for a long period of time and thus can accumulate in an increased concentration at the binding site.

In T2-weighted NMR tomography, the very small super-paramagnetic single-domain particles yield a good negative contrast for liver, spleen, bone marrow and lymph nodes.

The quantities of very small super-paramagnetic single-domain particles used are approx. 5 to 20 mM Fe/kg body weight when used as parenteral contrast media for NMR and approx. 10 mM Fe/kg body weight when used as an oral contrast medium.

What is claimed is:

1. Super-paramagnetic single-domain particles having an increased $R_1$ relaxivity and surface stabilizer substances, comprising particles of iron hydroxide, iron oxide hydrate, iron oxide, mixed iron oxides or iron having a particle size in the range between 1 and 10 nanometers, with an average particle diameter $d_{50}$ of two to four nanometers; having an increased $R_1$ relaxivity in the range of two to fifty, having a $R_2/R_1$ relaxivity ratio of less than five; and having at their surface first stabilizer substances selected from the group consisting of aliphatic dicarboxylic acids and aliphatic polycarboxylic acids, substitution products thereof and derivatives thereof, preventing aggregation and sedimentation of the stabilized particles in a gravitational field or in a magnetic field; and said aliphatic polycarboxylic acids being selected from the group consisting of citric acid, cyclohexanetricarboxylic acid, cyclohexanehexacarboxylic acid, ethylene-diaminetetraacetic acid and diethylenetriaminepentaacetic acid.

2. Super-paramagnetic particles according to claim 1, wherein particles, in addition to having first stabilizer substances selected from the group of aliphatic dicarboxylic acids and polycarboxylic acids, substitution products thereof and derivatives thereof at a surface, also have bound to said first stabilizer substances further stabilizer substances.

3. Super-paramagnetic particles according to claim 1, wherein the particle size of the super-paramagnetic single-domain particles is in the range of 1 to 5 nm, and said super-paramagnetic single-domain particles consist of iron hydroxide; iron oxide hydrate; $\gamma\text{-}Fe_2O_3$; $Fe_3O_4$; mixed iron oxides of the general formula $mMO.nFe_2O_3$, where M denotes the divalent metal ions Fe, Co, Ni, Mn, Be, Mg, Ca, Ba, Sr, Cu, Zn, Pt or mixtures thereof; mixed oxides of the general formula $mFe_2O_3.nMe_2O_3$, where Me denotes the trivalent metal ions Al, Cr, Bi, rare earth metals or mixtures thereof; or iron, where m and n are integers from 1 to 6.

4. Super-paramagnetic particles according to claim 1, wherein the super-paramagnetic single-domain particles have on their surface first stabilizer substances selected from the group consisting of malic acid, tartaric acid, citric acid, aspartic acid and mixtures thereof.

5. Super-paramagnetic particles according to claim 2, wherein the further stabilizer substances are selected from the group consisting of substances containing mono- and/or polyhydroxyl groups; aromatic substances containing mono- and/or polyhydroxyl groups; polycyclic condensed aromatic compounds and their derivatives containing phosphate groups, diphosphate groups, polyphosphate groups, thiophosphate groups, phosphonate groups, thiophosphonate groups, carboxylate groups, sulfate groups, mercapto groups or silanetriol groups; macromolecules containing amino acids; the thio group containing substances biotin, mercaptopurine, mercaptocytosine, mercaptocytosine, mercaptoguanine, mercaptouracil, mercaptothymine, mercaptohypoxanthine and their mercaptonucleosides and mercaptodeoxynucleosides; substances of ortho-silicic acid containing silicate groups and their condensation products with divalent and polyvalent inorganic ions, organic acids and bases; substances of ortho- or metaphosphoric acid containing phosphate groups as well as their condensation products and heterocondensation products and water-insoluble salt compounds with inorganic ions and organic compounds having basic groups; substances from the group of carbohydrates having phosphate groups, di-phosphate groups, polyphosphate groups, thiophosphate groups, phosphonate groups, thiophosphonate groups, carboxylate groups, sulfate groups, sulfonate groups, mercapto groups, silanetriol groups or trialkoxysilane groups; polyethylene glycols, polyalkylene glycols, alkyl polyethylene glycols, aryl polyethylene glycols, alkylaryl polyethylene glycols; block copolymers of polyethylene glycol (PEG) and polypropylene glycol (PPG); polysaccharides that contain nitrogen and their derivatives and denaturing products; nucleotides containing phosphate groups and their oligomers and polymers; and mixtures thereof.

6. A pharmacological preparation comprising a pharmacologically acceptable carrier and stabilized super-paramagnetic particles according to claim 1 with a particle size in the range between 1 and 10 nanometers.

7. A pharmacological preparation according to claim 6, wherein the stabilized super-paramagnetic particles are in combination with further stabilizer substances.

* * * * *